(12) United States Patent
Nandi et al.

(10) Patent No.: US 8,367,075 B2
(45) Date of Patent: Feb. 5, 2013

(54) SYNERGISTIC COMBINATION AND METHOD THEREOF

(75) Inventors: Dipankar Nandi, Bangalore (IN); Srabanti Rakshit, Bangalore (IN); Manikandan Ponnusamy, Chennai (IN)

(73) Assignee: Indian Institute of Science, Bangalore (IN)

( * ) Notice: Subject to any disclaimer, the term of this patent is extended or adjusted under 35 U.S.C. 154(b) by 0 days.

(21) Appl. No.: 13/173,833

(22) Filed: Jun. 30, 2011

(65) Prior Publication Data

US 2012/0003268 A1   Jan. 5, 2012

(30) Foreign Application Priority Data

Jul. 2, 2010   (IN) .......................... 1893/CHE/2010

(51) Int. Cl.
   *A61K 39/04*   (2006.01)
   *A61K 49/00*   (2006.01)
   *A61K 48/00*   (2006.01)

(52) U.S. Cl. ...... 424/248.1; 424/9.1; 424/9.2; 424/93.1; 424/93.4; 536/16.8

(58) Field of Classification Search .................. 424/9.1, 424/9.2, 93.1, 93.4, 248.1; 536/16.8
   See application file for complete search history.

*Primary Examiner* — Rodney P. Swartz
(74) *Attorney, Agent, or Firm* — Oliff & Berridge, PLC

(57) ABSTRACT

A method for the treatment of myeloma and thymoma by administering a therapeutically effective dose of *Mycobacterium indicus pranii* with Cyclophosphamide. This disclosure generally relates to the field of cancer biology. More specifically, this disclosure relates to the immunotherapeutic treatment of myeloma and thymoma, using a combination of heat killed *Mycobacterium indicus pranii* and the widely administered chemotherapeutic drug, Cyclophosphamide. *Mycobacterium indicus pranii* has already shown its efficacy as an immunomodulator and has been safely administered to humans. The most common method of cancer management is the application of chemotherapeutic drugs which results in side-effects. At lower non-toxic doses Cyclophosphamide is not effective. The present disclosure discloses a method of improving efficacy of non-toxic doses of Cyclophosphamide by administrating it together with *Mycobacterium indicus pranii*. This disclosure is relevant for the treatment of other lymphomas as well.

9 Claims, 15 Drawing Sheets

SYNERGISTIC COMBINATION AND METHOD THEREOF

This application claims priority to Indian Patent Application Publication No. 1893/CHE/2010 filed Jul. 2, 2010.

TECHNICAL FIELD

The present disclosure generally relates to the field of cancer biology. More specifically, this disclosure relates to the immunotherapeutic treatment of lymphomas, particularly myeloma and thymoma, using a combination of heat killed *Mycobacterium indicus pranii* (MIP) and chemotherapeutic drug, Cyclophosphamide. The instant disclosure also provides for a kit, method of manufacturing a kit and synergistic combination.

BACKGROUND AND PRIOR ART

Cancers which originate in the lymphatic system that comprises the bone marrow, spleen, thymus and lymph nodes are commonly termed "lymphomas" and account for about half of the blood cancers that occur each year.

A type of lymphoma is multiple myeloma which is characterized by the uncontrolled proliferation of malignant plasma cells in the bone marrow and production of monoclonal immunoglobulin detectable in serum and/or urine. Latest reports demonstrate early age of onset and increase in incidence, though the peak age of occurrence of multiple myeloma is 65 to 70 years of age. According to latest statistics, 1 to 5 per 100,000 individuals is afflicted each year worldwide with a greater incidence in the West. Men are more susceptible to myeloma and the overall incidence range varies from ~0.5-1/100,000 among Asians to as high as ~10-12/100,000 among African-American men. It is the second most prevalent hematologic malignancy in the United States, and it is estimated that ~20,580 men and women (11,680 men and 8,900 women) was diagnosed with and ~10,580 men and women died of myeloma in 2009 (NCI, NIH). The most common manifestation of the disease is bone destruction due to increased osteoclastic bone resorption and decreased bone formation. The median overall survival for myeloma patients is 4 to 5 years, ranging from <6 months to >10 years according to distinct prognostic factors.

Currently, the two most efficacious treatment options for patients with multiple myeloma are tandem high-dose chemotherapy, followed by autologous stem cell infusion, or allogeneic hematopoietic stem cell transplantation after myeloablative therapy. A choice among different chemotherapeutic drug combinations happens to be the first-line therapy in patients with refractory or relapsed disease or who might face complications with autologous stem cell transplantation. Commonly used agents either alone or in combination include Dexamethasone, Vincristine, Doxorubicin, Melphalan, Cyclophosphamide, Etoposide, and Cisplatin. New agents such as the immunomodulatory drugs Thalidomide and Lenalidomide, and the proteasome inhibitor Bortezomib, have been introduced for the treatment of relapsed multiple myeloma and have shown to induce significant recovery in patients. Moreover, the efficacy of chemotherapeutic drugs combined with stem cell transplantation did not meet expectations due to high levels of toxicity. Nevertheless, complete cure is very rarely achieved due to persistence of residual disease. Therefore, there is an urgent need for the development of promising new therapeutic candidates.

Another type of lymphoma is thymoma that arises from the thymus gland, usually with an indolent growth pattern; however, local invasion and/or metastases may occur. This tumor is associated with unique paraneoplastic syndromes (myasthenia gravis, pure red cell aplasia, hypogammaglobulinemia and other autoimmune diseases). The overall incidence of thymoma is rare; with 0.15 cases per 100,000 and account for only 0.2% to 1.5% of all the malignancies. Thymomas have been found to occur at all ages, from patients of 8 months to 90 years with a mean age of about 53 years and have equal gender distribution. Locally advanced thymoma requires a multimodality treatment approach with a combination of surgery, chemotherapy and radiation therapy to reduce the chances of recurrence and improve survival. The common chemotherapeutic drugs used for the treatment of thymoma include: cyclophosphamide, doxorubicin, etoposide, cisplatin and paclitaxel. Hormonal therapy is also occasionally applied that involves corticosteroids.

The limitations of using multiple and high dose of chemotherapeutic drugs are elevated levels of toxicity which leads to harmful side-effects. Moreover, relapse is also common due to resistance to these drugs.

In the last decade, cancer immunotherapy has emerged as the new therapeutic option for multiple myeloma patients otherwise unresponsive to traditional modes of cancer therapy or as combination therapy to reduce the harmful effects of other cancer treatments. Tumor immunotherapy based approach stimulates the innate and adaptive cells of the host immune system for efficient induction and maintenance of endogenous anti-tumor immune responses necessary to recognize and eradicate malignant tissue. Moreover, immunosuppressive cells such as regulatory T cells or myeloid suppressor cells produced by the myeloma needs to be eliminated for success of cancer immunotherapy.

Different bacteria belonging to the *Mycobacterium* family display remarkable adjuvant properties and modulate the host immune response. Heat-killed saprophytic mycobacteria such as *Mycobacterium vaccae* and related members have been found to be effective and are being currently exploited in ongoing clinical trials. Another *mycobacterium* that has been widely used as adjunct to multi-drug therapy in leprosy is *Mycobacterium w*, currently known as MIP. Unlike BCG, MIP retains its immunologic potential even after it is killed. Both in vitro and in viva studies have shown that killed MIP enhances immune responses to *Mycobacterium leprae* antigens. Recent studies have shown that MIP is effective in the therapy of other chronic diseases such as tuberculosis, HIV infection, cancer, psoriasis and bronchial asthma.

To date, myeloma remains a lethal disease even though huge progress has been made in understanding its pathophysiology and biology and advent of new aggressive chemotherapeutic drugs. Unfortunately, myeloma largely remains incurable with a history of relapse in majority of patients and complete remissions are still rare. Similarly, thymoma also has a high incidence of recurrence with increased risk of having another type of cancer and metastasis to other organs. Hence, lifelong follow-up after surgical removal of thymoma is necessary. Moreover, the toxicity of anticancer agents such as Cyclophosphamide, one of the most common drugs used in the treatment of various cancers, continues to pose a problem for the use of these chemotherapeutic agents. In addition, extrapolation of in vitro studies to treatment regimens for cancer patients has its share of inherent difficulties. Accordingly, it would be beneficial to develop new approaches that can selectively prevent the toxic side effects of Cyclophosphamide such as bladder and cardiac toxicity and hair loss and at the same time has the potential to maintain or enhance its therapeutic efficacy.

STATEMENT OF THE DISCLOSURE

Accordingly, the present disclosure relates to a synergistic sequential combination comprising *Mycobacterium indicus pranii* (MIP) and Cyclophosphamide for treatment of lymphoma, wherein the *Mycobacterium indicus pranii* is added about 24 hours prior to Cyclophosphamide; and a method of treating lymphoma, said method comprising step of administering a synergistic sequential combination comprising *Mycobacterium indicus pranii* (MIP) about 24 hours prior to administration of Cyclophosphamide, to a subject in need thereof.

BRIEF DESCRIPTION OF ACCOMPANYING FIGURES

In order that the disclosure may be readily understood and put into practical effect, reference will now be made to exemplary embodiments as illustrated with reference to the accompanying figures. The figure together with a detailed description below, are incorporated in and form part of the specification, and serve to further illustrate the embodiments and explain various principles and advantages, in accordance with the present disclosure where:

FIG. 4A, B and C shows the standardization of doses of Cyclophosphamide, Indomethacin and RU486 in the Sp2/0 tumor model.

FIG. 5A shows the experimental outline for the comparison of the combination of different drugs and $5\times10^8$ *Mycobacterium indicus pranii* in the Sp2/0 myeloma model.

FIG. 5B shows the comparative efficacy of the combination of different drugs and $5\times10^8$ *Mycobacterium indicus pranii* in Sp2/0 myeloma bearing mice.

FIG. 5C shows the maximum reduction in tumor volume when mice are administered with *Mycobacterium indicus pranii* and cyclophosphamide.

Figure 6:
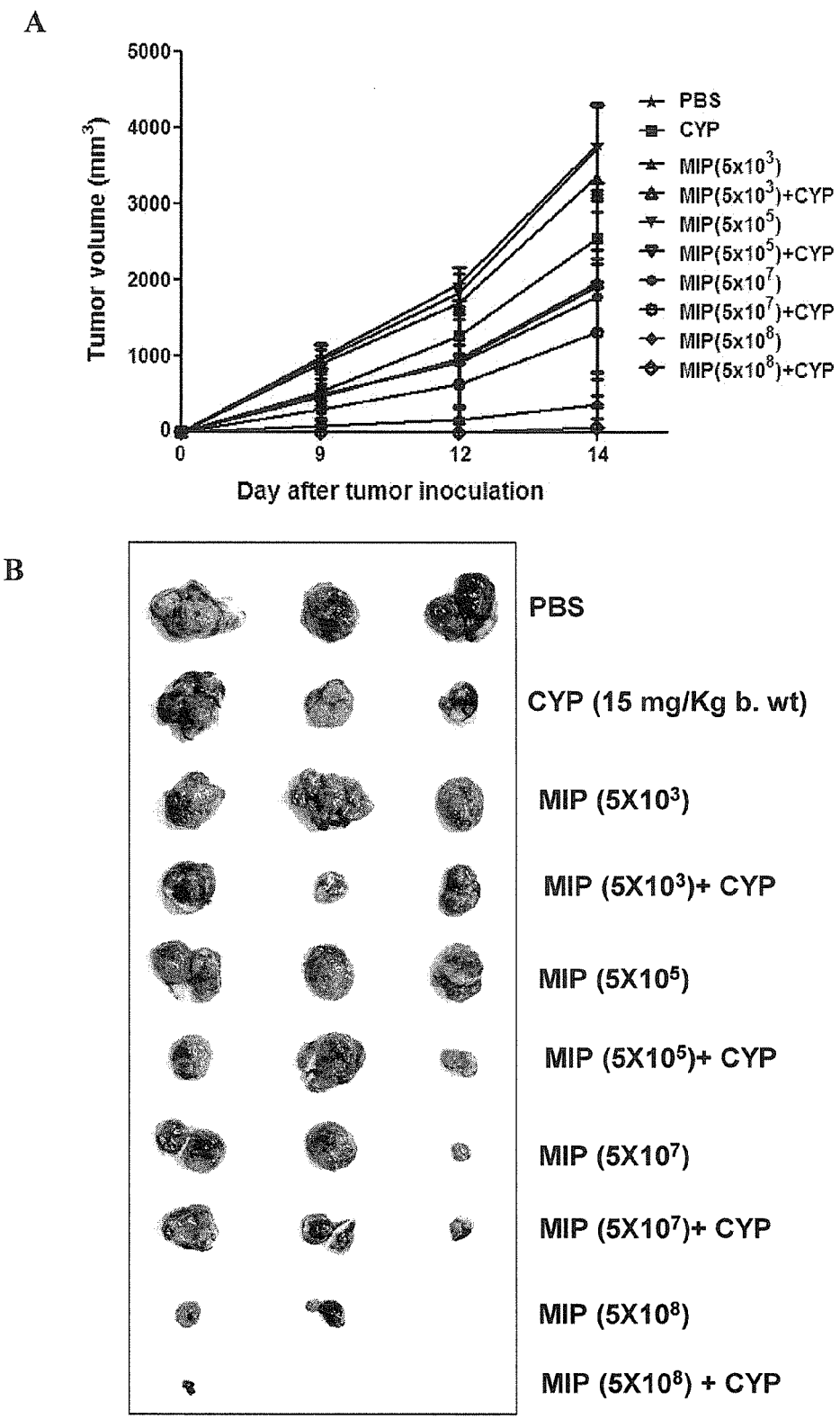

FIG. 6A shows comparative efficacy of different doses of *Mycobacterium indicus pranii* and fixed dose of 15 mg/kg b. wt cyclophosphamide per mouse administered at day 3 and day 4 respectively in Sp2/0 myeloma bearing mice.

FIG. 6B shows the pictographs depicting the size of the isolated subcutaneous solid myeloma tumors after treatment with different doses of *Mycobacterium indicus pranii* and fixed dose of 15 mg/kg b. wt cyclophosphamide per mouse administered at day 3 and day 4 respectively in Sp2/0 myeloma bearing mice.

Figure 7:
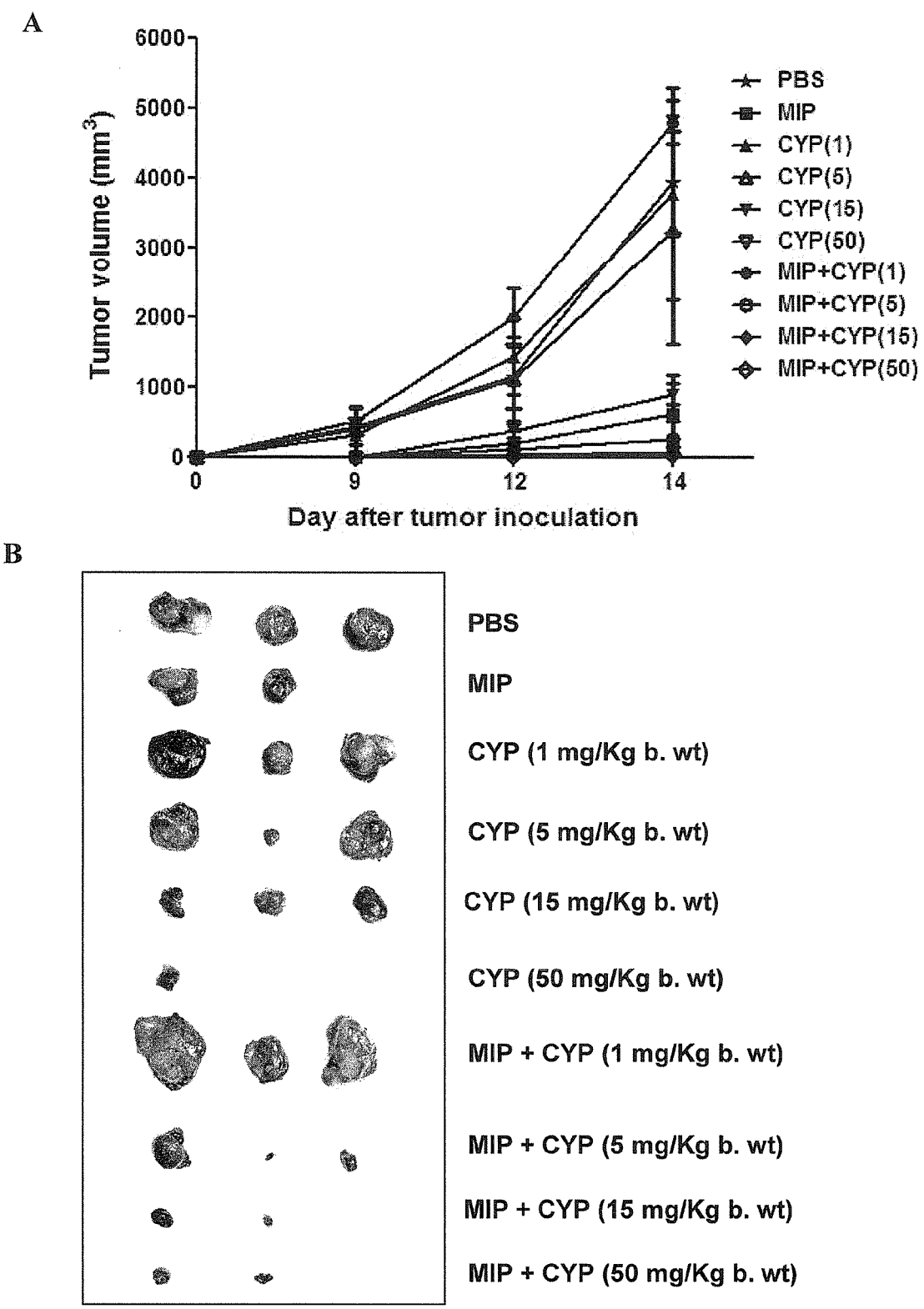

FIG. 7A shows comparative efficacy of different doses of cyclophosphamide and fixed dose of $5\times10^8$ *Mycobacterium indicus pranii* administered at day 4 and day 3 respectively in Sp2/0 myeloma bearing mice.

FIG. 7B shows the pictographs depicting the size of the isolated subcutaneous solid myeloma tumors after treatment with different doses of cyclophosphamide and fixed dose of $5\times10^8$ *Mycobacterium indicus pranii* administered at day 4 and day 3 respectively in Sp2/0 myeloma bearing mice.

Figure 8:
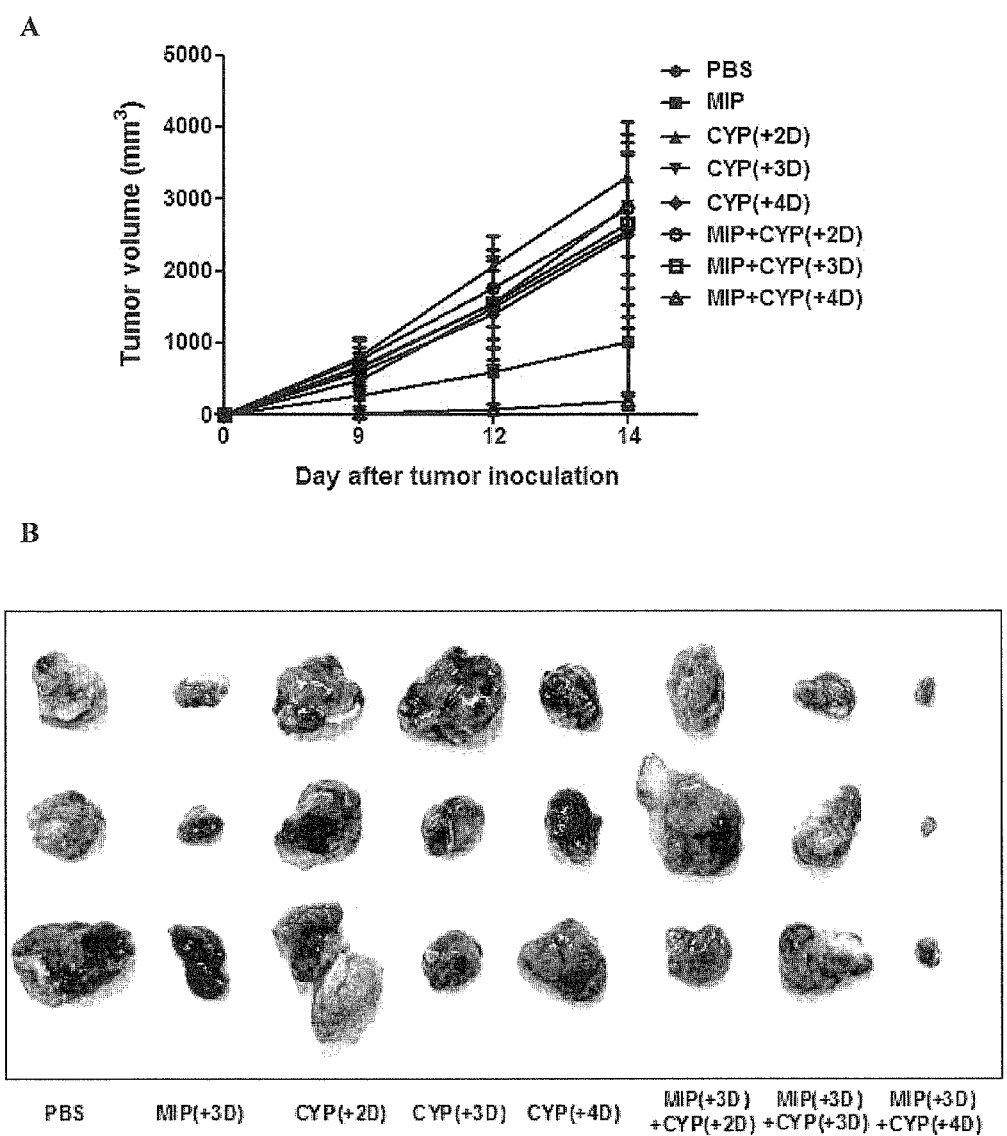

FIG. 8A shows comparative efficacy of different days of administration of 15 mg/kg b. wt cyclophosphamide and $5\times10^8$ *Mycobacterium indicus pranii* in Sp2/0 myeloma bearing mice.

FIG. 8B shows the pictographs depicting the size of the isolated subcutaneous solid myeloma tumors after treatment with cyclophosphamide on different days and *Mycobacterium indicus pranii* in Sp2/0 myeloma bearing mice.

Figure 9:
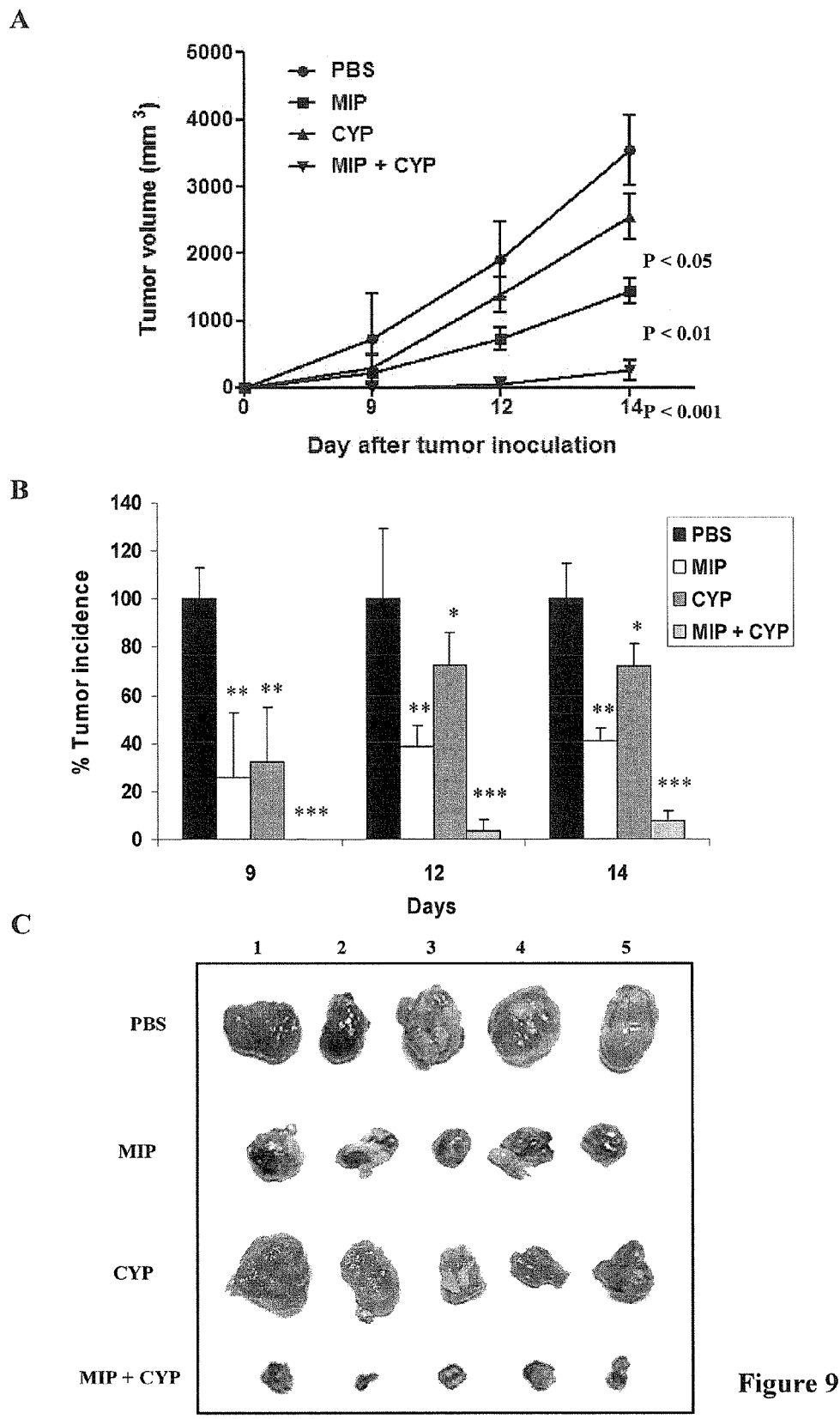
Figure 9:
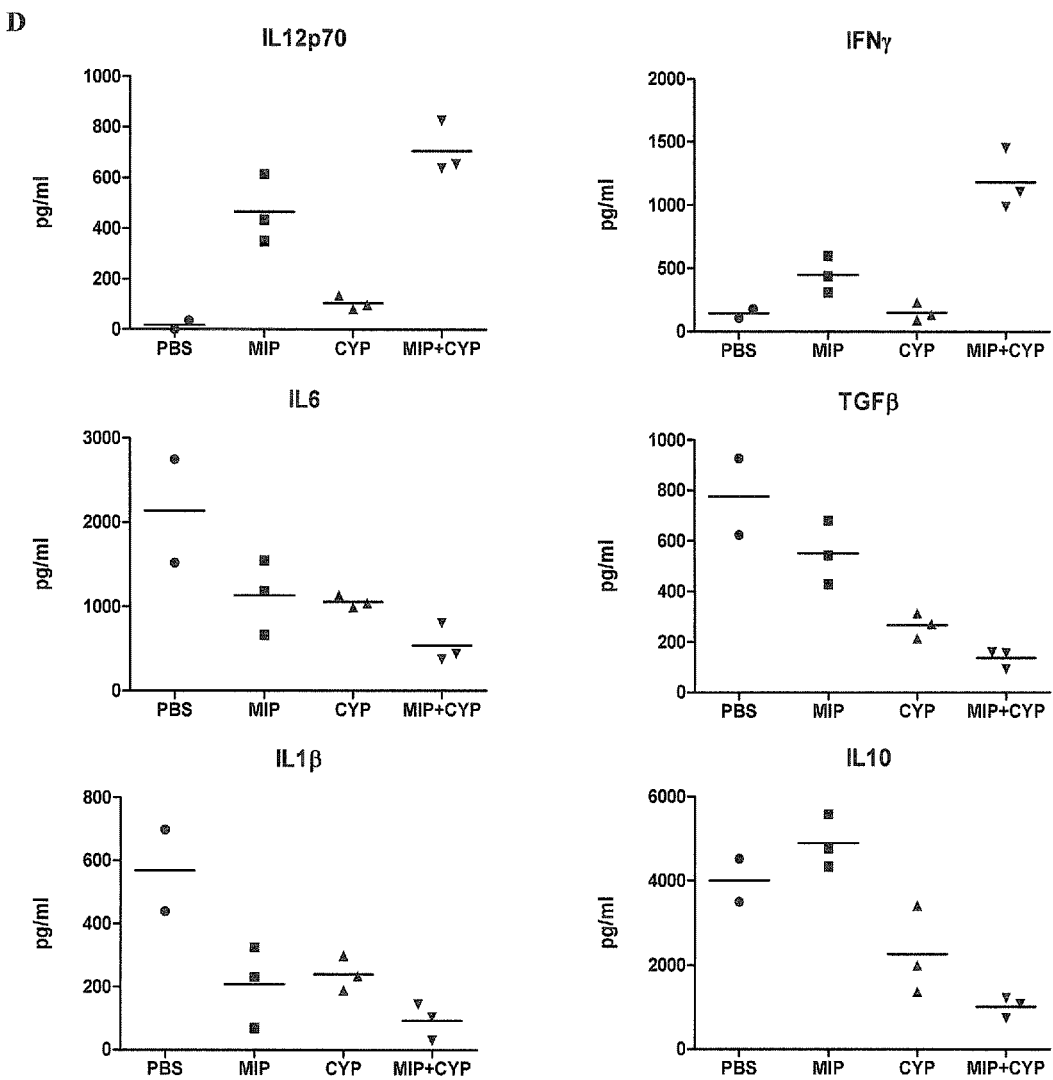

FIG. 9A shows the estimation of tumor volume on the $9^{th}$, $12^{th}$ and $14^{th}$ day after tumor inoculation in Sp2/0 myeloma bearing mice administered with $5\times10^8$ *Mycobacterium indicus pranii*, and 15 mg/kg b. wt Cyclophosphamide at day 3 and day 4 respectively.

FIG. 9B shows the maximum reduction in tumor volume when mice are administered with $5\times10^8$ *Mycobacterium indicus pranii* at day 3 in combination with 15 mg/kg b. wt Cyclophosphamide at day 4.

FIG. 9C shows the pictographs depicting the size of the isolated subcutaneous solid myeloma tumors after treatment with PBS, *Mycobacterium indicus pranii*, Cyclophosphamide and a combination of *Mycobacterium indicus pranii* along with Cyclophosphamide.

FIG. 9D shows the cytokine production upon combination therapy of myeloma with *Mycobacterium indicus pranii* and Cyclophosphamide.

Figure 10:
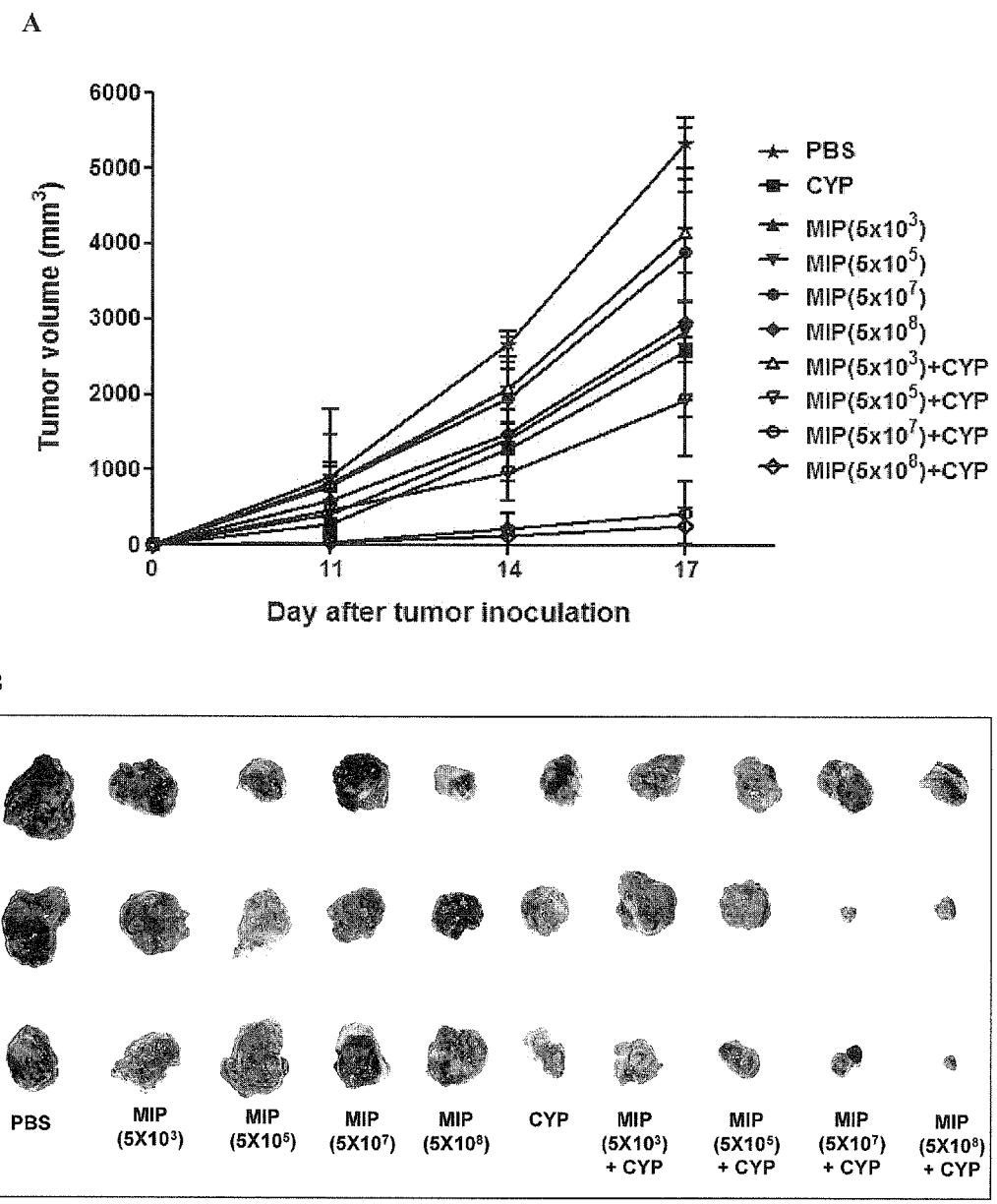

FIG. 10A shows comparative efficacy of different doses of *Mycobacterium indicus pranii* and fixed dose of 15 mg/kg b. wt cyclophosphamide per mouse administered at later time points, i.e. day 7 and day 8 respectively in Sp2/0 myeloma bearing mice.

FIG. 10B shows the pictographs depicting the size of the isolated subcutaneous solid myeloma tumors after treatment with different doses of *Mycobacterium indicus pranii* and fixed dose of 15 mg/kg b. wt cyclophosphamide per mouse administered at day 7 and day 8 respectively in Sp2/0 myeloma bearing mice.

Figure 11:
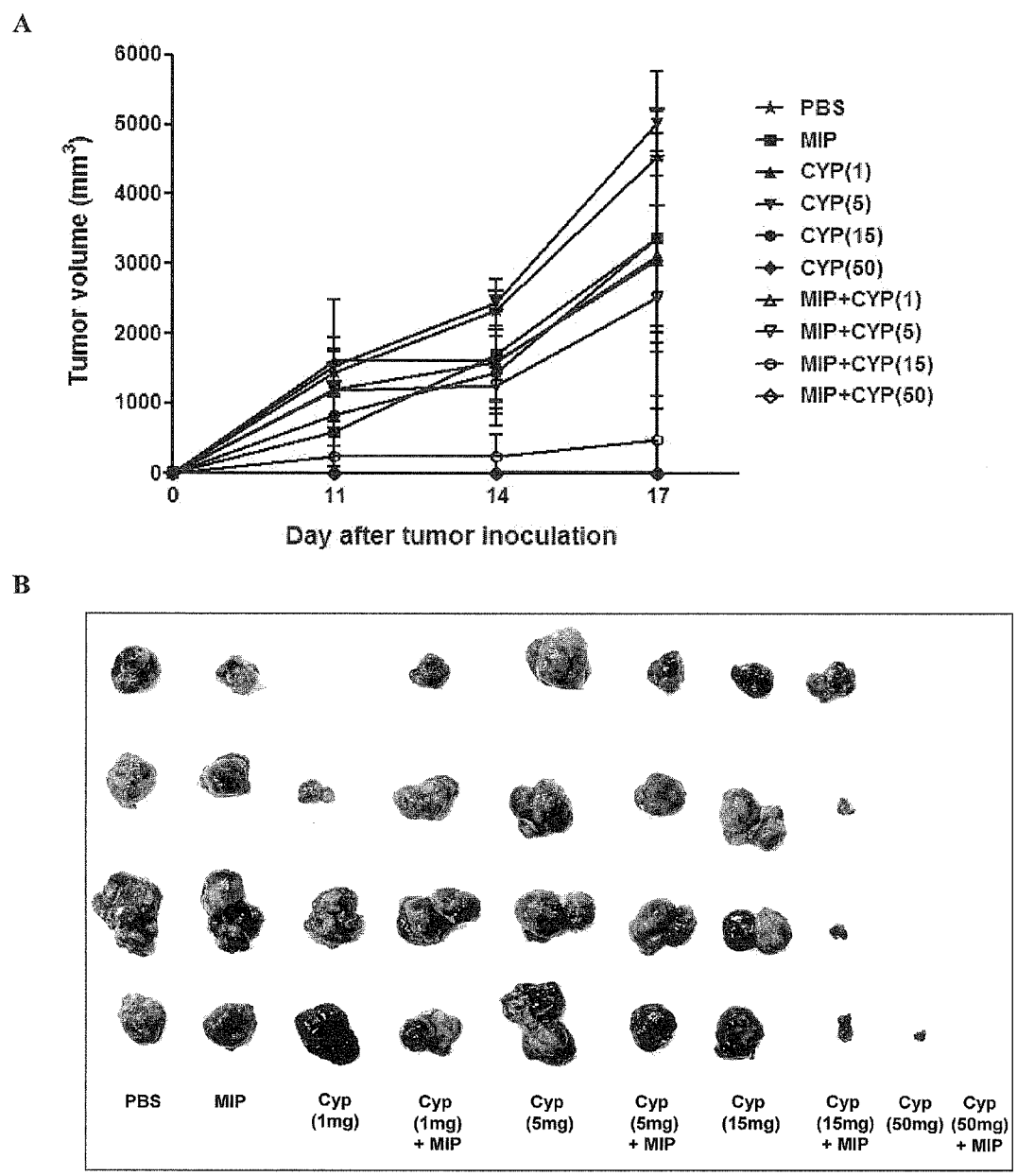

FIG. 11A shows comparative efficacy of different doses of cyclophosphamide and fixed dose of $5\times10^8$ *Mycobacterium indicus pranii* per mouse administered at day 8 and day 7 respectively in Sp2/0 myeloma bearing mice.

FIG. 11B shows the pictographs depicting the size of the isolated subcutaneous solid myeloma tumors after treatment with different doses of cyclophosphamide and fixed dose of $5\times10^8$ *Mycobacterium indicus pranii* per mouse administered at day 8 and day 7 respectively in Sp2/0 myeloma bearing mice.

Figure 12:
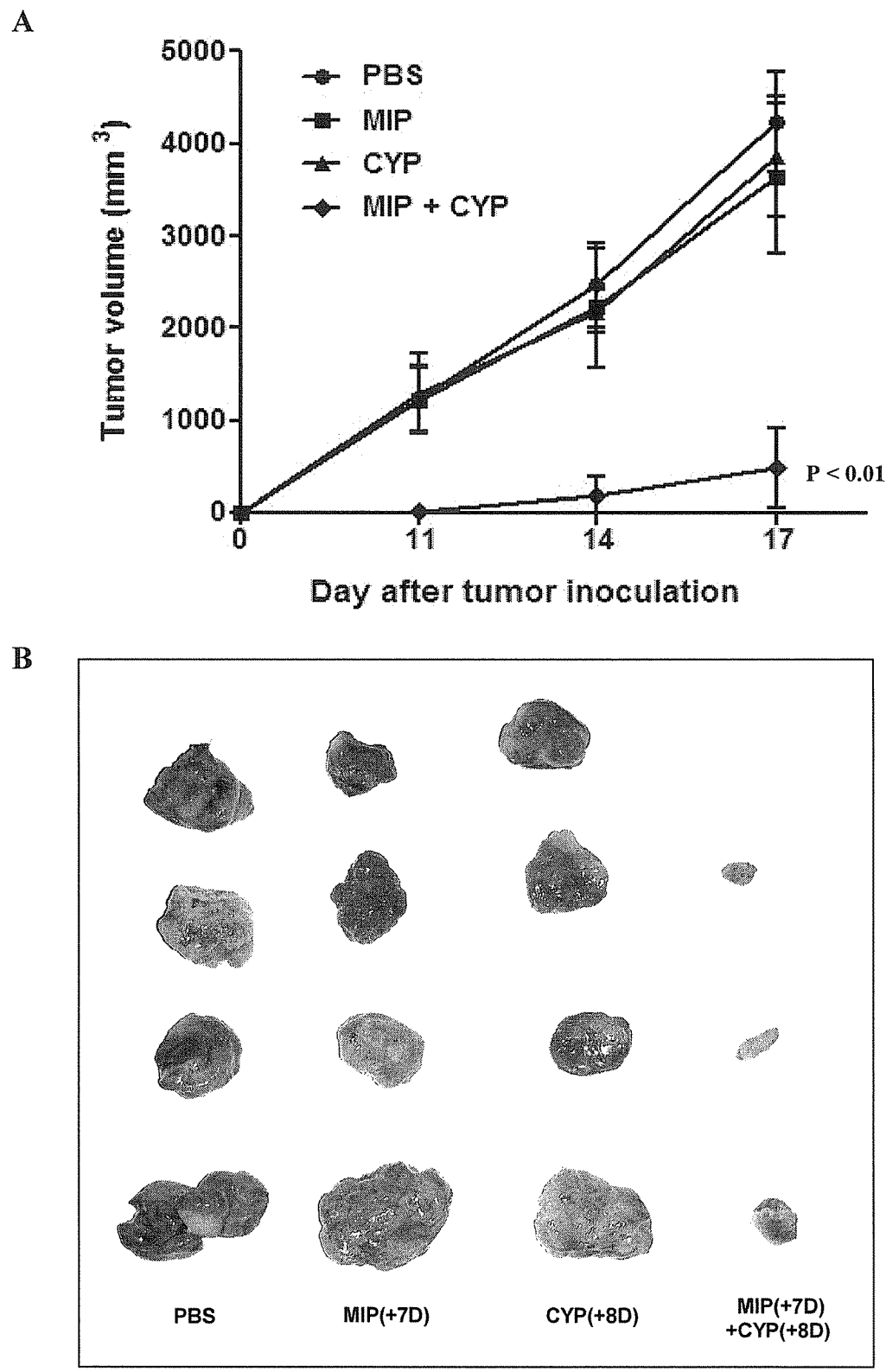

FIG. 12A shows the estimation of tumor volume on the $11^{th}$, $14^{th}$ and $17^{th}$ day after tumor inoculation in Sp2/0 myeloma bearing mice administered with $5\times10^8$ *Mycobacterium indicus pranii* and 15 mg/kg b. wt Cyclophosphamide at day 7 and day 8 respectively.

FIG. 12B shows the pictographs depicting the size of the isolated subcutaneous solid myeloma tumors after treatment with PBS, *Mycobacterium indicus pranii*, Cyclophosphamide and a combination of *Mycobacterium indicus pranii* along with Cyclophosphamide.

Figure 13:
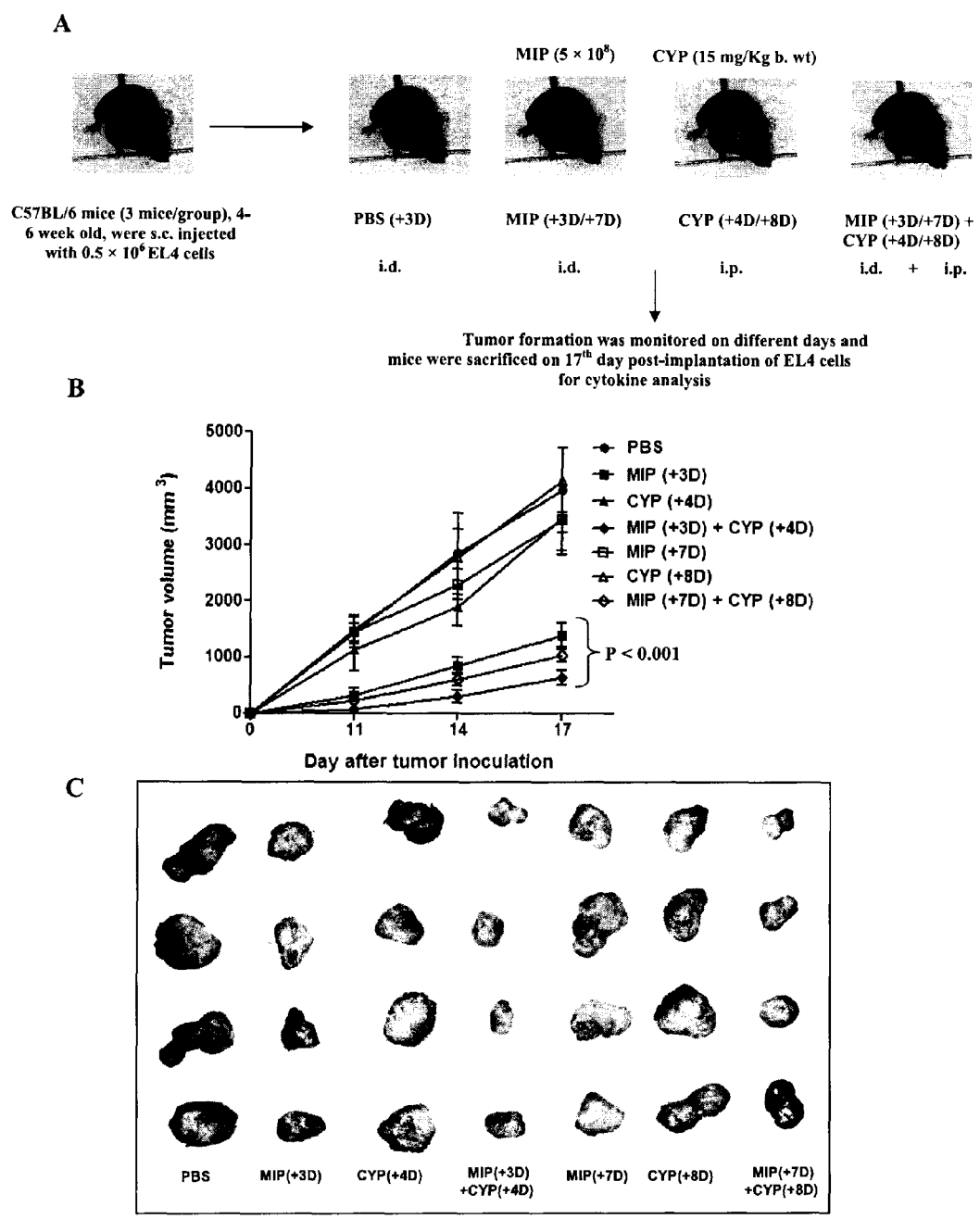
Figure 13:
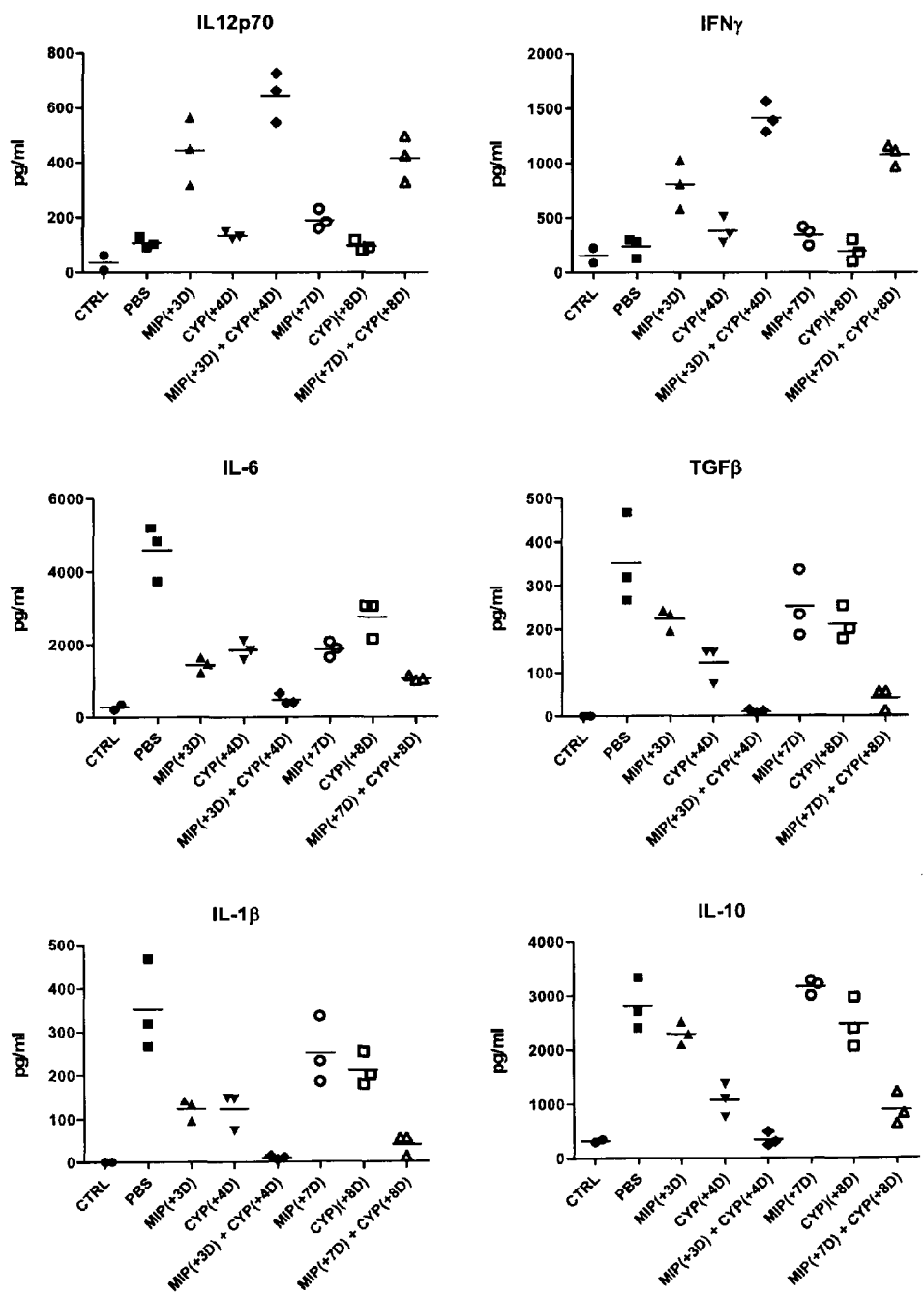

FIG. 13A shows the experimental outline in the EL4 thymoma model.

FIG. 13B shows the estimation of tumor volume on the $11^{th}$, $14^{th}$ and $17^{th}$ day after tumor inoculation in EL4 thymoma bearing mice administered with $5\times10^8$ *Mycobacterium indicus pranii* and 15 mg/kg b. wt Cyclophosphamide at day 3/7 and day 4/8 respectively.

FIG. 13C shows the pictographs depicting the size of the isolated subcutaneous solid myeloma tumors after treatment with PBS, *Mycobacterium indicus pranii*, Cyclophosphamide and a combination of *Mycobacterium indicus pranii* along with Cyclophosphamide at early and late stages of tumor growth.

FIG. 13D shows the cytokine production upon combination therapy of thymoma with *Mycobacterium indicus pranii* and Cyclophosphamide.

DETAILED DESCRIPTION OF THE DISCLOSURE

The present disclosure relates to a synergistic sequential combination comprising *Mycobacterium indicus pranii* (MIP) and Cyclophosphamide for treatment of lymphoma, wherein the *Mycobacterium indicus pranii* is added about 24 hours prior to Cyclophosphamide.

In an embodiment of the present disclosure, the *Mycobacterium indicus pranii* is heat killed bacteria at concentration ranging from about $5 \times 10^7$ to about $5 \times 10^9$ of *Mycobacterium* cells, preferably about $5 \times 10^8$ of *Mycobacterium* cells; and wherein the Cyclophosphamide is at non-toxic low dose ranging from about 5 mg/Kg body weight to about 25 mg/Kg body weight, preferably about 15 mg/Kg body weight.

In another embodiment of the present disclosure, the synergistic sequential combination of the *Mycobacterium indicus pranii* with the Cyclophosphamide improves efficacy of non-toxic dose of the Cyclophosphamide as compared to the Cyclophosphamide alone.

In yet another embodiment of the present disclosure, the synergistic sequential combination acts as an immunomodulator modulating cytokine amounts in sera during Myeloma.

In still another embodiment of the present disclosure, the combination is in form of a Kit, optionally along with pharmaceutically acceptable excipients and instruction manual. The present disclosure relates to a method of treating lymphoma, said method comprising step of administering a synergistic sequential combination comprising *Mycobacterium indicus pranii* (MIP) about 24 hours prior to administration of Cyclophosphamide, to a subject in need thereof.

In an embodiment of the present disclosure, the synergistic sequential combination is a formulation capable of releasing *Mycobacterium indicus pranii* about 24 hours prior to the Cyclophosphamide.

In another embodiment of the present disclosure, the subject is a mammal including human being.

In yet another embodiment of the present disclosure, the *Mycobacterium indicus pranii* is heat killed bacteria at concentration ranging from about $5 \times 10^7$ to about $5 \times 10^9$ of *Mycobacterium* cells, preferably about $5 \times 10^8$ of *Mycobacterium* cells; and wherein the Cyclophosphamide is at non-toxic low dose ranging from about 5 mg/Kg body weight to about 25 mg/Kg body weight, preferably about 15 mg/Kg body weight.

In still another embodiment of the present disclosure, the *Mycobacterium indicus pranii* is administered intradermally and the Cyclophosphamide is administered intraperitoneally.

In still another embodiment of the present disclosure, the lymphoma is selected from a group comprising Myeloma and Thymoma.

In still another embodiment of the present disclosure, the synergistic sequential combination of the *Mycobacterium indicus pranii* with the Cyclophosphamide improves efficacy of non-toxic dose of the Cyclophosphamide as compared to the Cyclophosphamide alone.

In still another embodiment of the present disclosure, the improvement in the efficacy is ranging from about 6 to about 7 fold and reduction in tumor size is ranging from about 80% to about 90% as compared to Phosphate Buffer Saline alone.

Overall, the method as claimed wherein the improvement in the efficacy is observed at both early and late stages of lymphoma.

In an embodiment of the present disclosure, *Mycobacterium indicus pranii* can be safely given to patients without having to go through various clinical trials as it has been previously administered to human beings suffering from different ailments where it has shown no adverse side effects. Thus, the present disclosure relates to the combined application of *Mycobacterium indicus pranii*, possibly acting as an immunoadjuvant, with drugs like Cyclophosphamide in myeloma and thymoma tumor models to evaluate their synergistic effect on tumor regression by reducing the harmful side-effects.

The present disclosure relates to a combination administration of heat killed microorganism along with Cyclophosphamide for the treatment of lymphomas and efficacy is shown in myeloma and thymoma. This administration of *Mycobacterium indicus pranii* and Cyclophosphamide is in a sequential order. The combination of Cyclophosphamide along with *Mycobacterium indicus pranii* is effective for the treatment of lymphomas such as myeloma and thymoma when administered at an effective concentration dosage value.

In an embodiment of the present disclosure, *Mycobacterium indicus pranii* is injected via intradermal route and Cyclophosphamide is administered via intraperitoneal route the following day. The intradermal route of injection is selected based on the route administered to humans. Intraperitoneal route of *Mycobacterium indicus pranii* administration did not produce any beneficial effect on tumor reduction (data not shown). *Mycobacterium indicus pranii* injection boosts the antitumor responses of immune system, most likely, by acting as an adjuvant and Cyclophosphamide injected one day later further enhances the anti-tumor effect on the developing myeloma or thymoma. Cyclophosphamide is given one day after MIP administration to boost the antitumor activity of MIP, thereby enhancing the immune response of the host required for tumor eradication.

In another embodiment of the present disclosure, a reduction in tumor volume is observed as substantiated by the examples below, when 0.1 ml of vaccine containing ~$5 \times 10^8$ of said *Mycobacterium* is intradermally injected to mice three or seven days after inoculation of tumor cells and Cyclophosphamide of 15 mg/Kg body weight amount is injected one day after. Hence, it can be derived that even after detection of the tumor, administration of sequential combination of Cyclophosphamide and *Mycobacterium indicus pranii* to a subject in need would result in substantial reduction of tumor. This aspect is extremely important due to its clinical relevance.

The present disclosure is further described with the help of the following examples and figures. However, these examples should not be construed to limit the scope of the disclosure.

Example 1

Standardization of Dose of Sp2/0 Myeloma Cells Required to Induce Solid Subcutaneous Tumors in BALB/c Mice BALB/c male mice, aged 6-8 weeks and weighing ~18-25 g, are procured from the Central Animal Facility, Indian Institute of Science, Bangalore. All mice received care according to institutional guidelines and are maintained under controlled conditions and fed with a standard diet.

Sp2/0 cells, a myeloma cell line, is grown in T175 flasks in IMDM complete medium supplemented with 10% fetal bovine serum, 2 mM L-glutamine, 100 U/ml penicillin, 100 μg/ml streptomycin, 10% nonessential amino acids, 10% HEPES, 10% sodium pyruvate, 50 μM 2-ME, 10 μg/ml gentamycin in a humidified atmosphere of 5% $CO_2$ at 37° C.

An experimental syngeneic tumor model using the myeloma, Sp2/0 in BALB/c mice is studied. Sp2/0 cells injected subcutaneously (s.c) develop tumors and is used as an in vivo model for tumorigenesis. Different amounts of cells are washed and injected s.c. to establish the cell numbers that need to be injected to reproducibly display solid tumors within two weeks. Mice are sacrificed once the tumors reach a large size to avoid distress. Tumor volume is monitored on the mentioned days and calculated with the formula, $V=a \times b^2/2$, where a is the longest and b is perpendicular to it, are measured on the surface of the tumor with vernier calipers.

Figure 1:
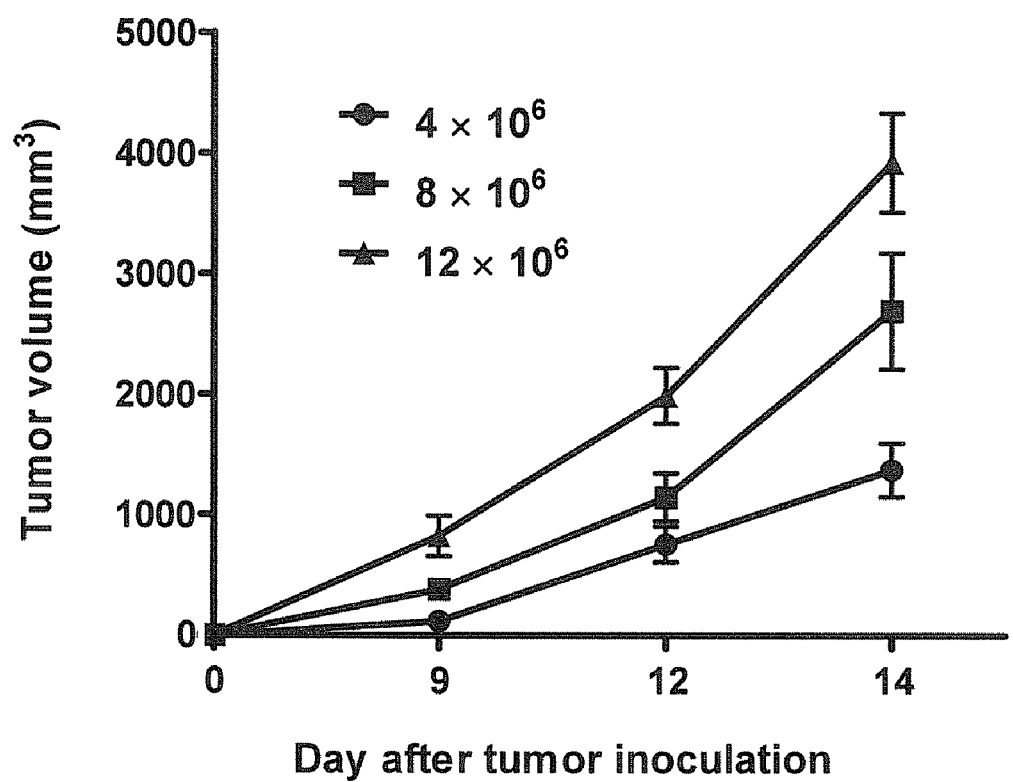
FIG. 1 shows standardization of the dose of Sp2/0 myeloma cells for the development of tumor in BALB/c mice.

The standardization of the dose of Sp2/0 myeloma cells for the development of tumor in BALB/c mice is depicted in FIG. 1. BALB/c mice (5 per group) of 6 to 8 weeks of age are subcutaneously injected with different doses of Sp2/0 myeloma cells ($4 \times 10^6$, $8 \times 10^6$ and $12 \times 10^6$). The tumor volume is estimated on the $9^{th}$, $12^{th}$ and $14^{th}$ day after tumor inoculation is done.

Early log phase Sp2/0 myeloma cells are more efficient in inducing solid tumors in BALB/c mice by 8 days post-injection whereas late log phase cells are unable to induce any tumor. An injection of about 10 to $12 \times 10^6$ Sp2/0 cells appears to be the optimal dose for the generation of tumors in mice.

Example 2

Comparative Efficacy Between the Prophylactic and Therapeutic Mode of Treatment of Sp2/0 Myeloma by *Mycobacterium Indicus Pranii*

Immunoprophylactic and immunotherapeutic mode of *Mycobacterium indicus pranii* administration to BALB/c mice bearing Sp2/0 tumors are compared by injecting *Mycobacterium indicus pranii* intradermally one day prior to or 3 and 6 days after Sp2/0 cell implantation. Tumor volume is measured kinetically for monitoring the growth of Sp2/0 tumors. Phosphate Buffered Saline (PBS) is intradermally injected into control mice.

Figure 2:
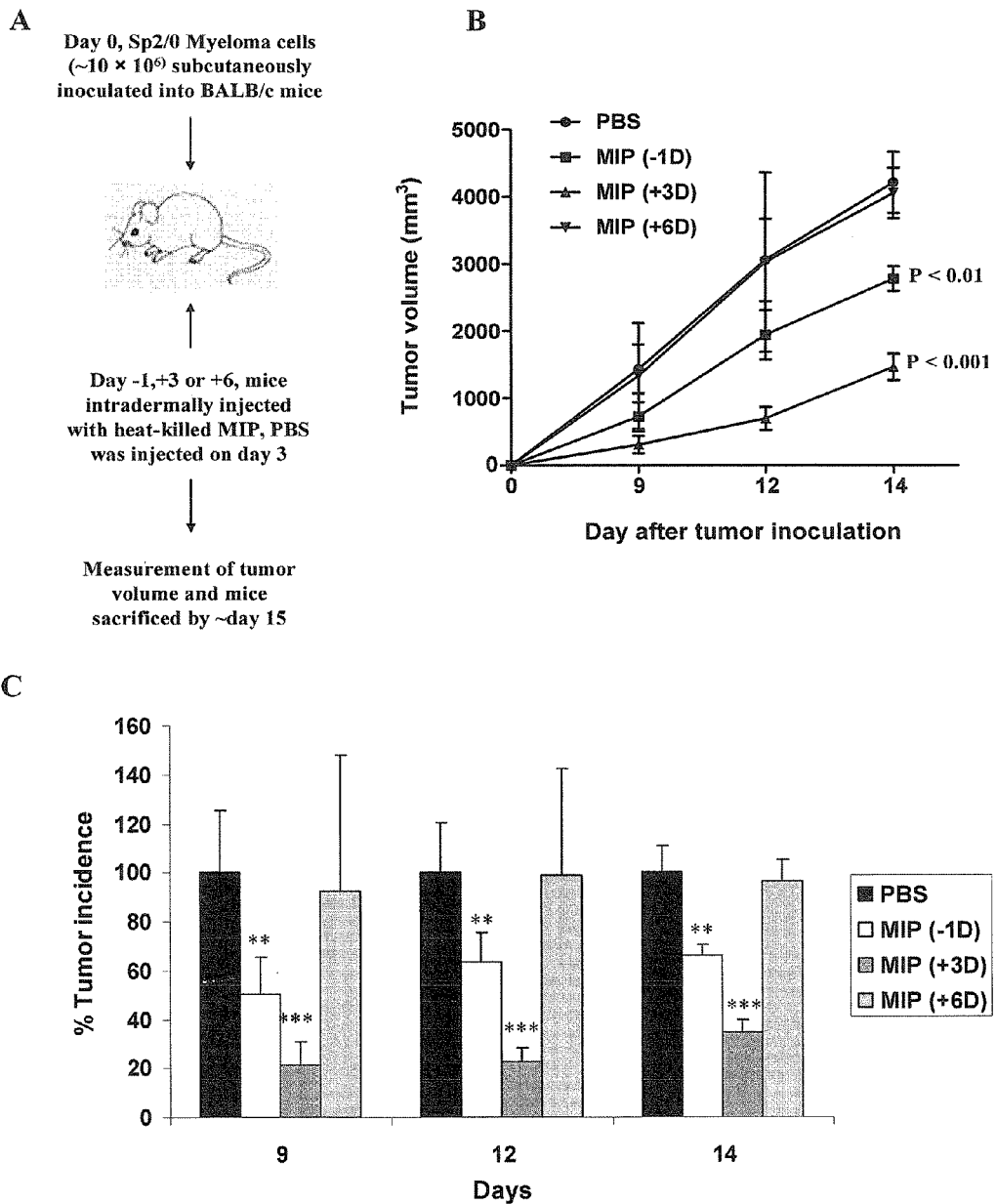
FIG. 2A shows the experimental outline in the Sp2/0 myeloma model.
FIG. 2B shows in vivo efficacy of *Mycobacterium indicus pranii* (MIP) alone in Sp2/0 myeloma model.
FIG. 2C shows the maximum reduction in tumor volume when mice are administered with *Mycobacterium indicus pranii* alone at day 3 post-inoculation of Sp2/0 cells.

The FIG. 2 depicts in vivo efficacy of *Mycobacterium indicus pranii* (MIP) on Sp2/0 myeloma model. BALB/c mice (5 per group) of 6 to 8 weeks of age are subcutaneously injected with Sp2/0 myeloma cells (~$10 \times 10^6$ cells/mouse). Thereafter, mice are intradermally injected with *Mycobacterium indicus pranii* (~$5 \times 10^8$) either 1 day prior to or 3 or 6 days post-inoculation of tumor cells. Tumor volume is estimated on $9^{th}$, $12^{th}$ and $14^{th}$ day of tumor inoculation. Vehicle alone (0.1 ml of PBS) is used as control and intradermally injected 3 days after administration of cells.

Intra dermal injection of *Mycobacterium indicus pranii* is found to reduce the tumor size and is more effective when given therapeutically 3 days after injection of Sp2/0 cells. Overall, the data demonstrates that *Mycobacterium indicus pranii* efficiently reduced tumor formation and the immunotherapeutic treatment is more effective compared to immunoprophylactic treatment.

Example 3

Comparative Efficacy of Different Doses of *Mycobacterium Indicus Pranii*

Figure 3:
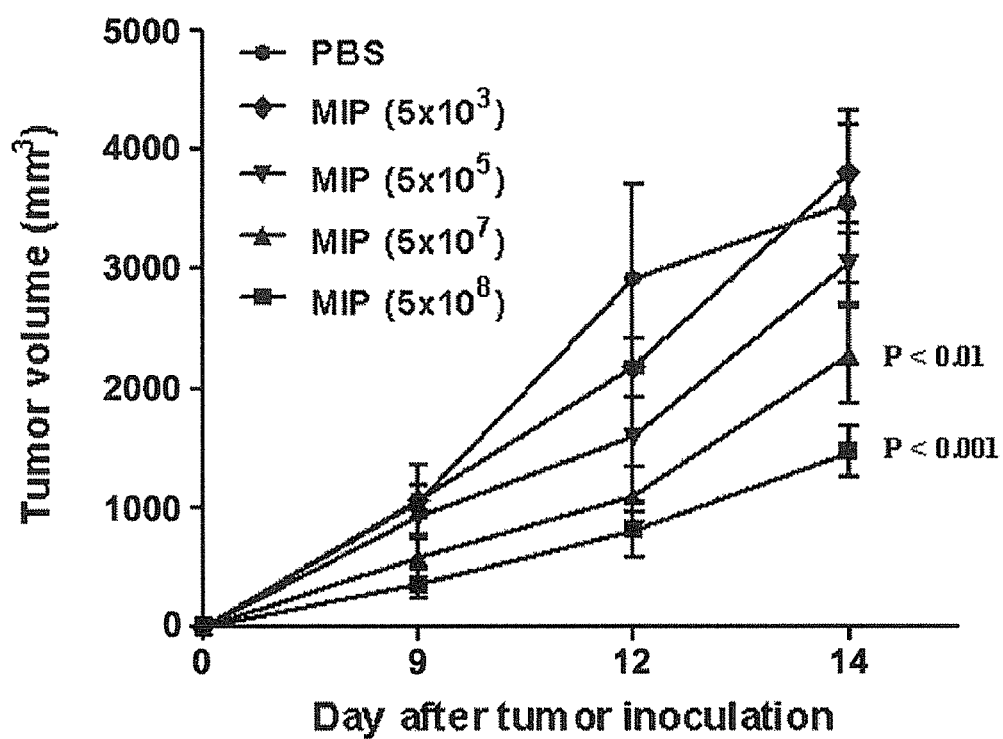
FIG. 3 shows comparative efficacy of different doses of *Mycobacterium indicus pranii* alone in Sp2/0 myeloma bearing mice.

Next, the optimum dose of *Mycobacterium indicus pranii* required for reducing the tumor size and delaying the appearance of tumors is titrated. Comparative efficacy of different doses of *Mycobacterium indicus pranii* in Sp2/0 myeloma bearing mice is provided in FIG. 3. BALB/c mice (5 per group) of 6 to 8 weeks of age are subcutaneously injected with Sp2/0 Myeloma cells (~$10 \times 10^6$ cells/mouse). Mice are intradermally injected with different doses of *Mycobacterium indicus pranii* ($5 \times 10^3$, $5 \times 10^5$, $5 \times 10^7$ and $5 \times 10^8$) 3 days post-inoculation of tumor cells. Tumor volume is estimated on the $9^{th}$, $12^{th}$ and $14^{th}$ day of tumor inoculation. Vehicle alone (0.1 ml of PBS) is used as control and intradermally injected 3 days after administration of cells. The effect of *Mycobacterium indicus pranii* is dose dependent and maximum reduction in tumor volume is observed when mice are administered with ~$5 \times 10^8$ *Mycobacterium indicus pranii*.

Example 4

Standardization of the Dose of Chemotherapeutic Drugs: Cyclophosphamide, Indomethacin and RU486

Figure 4:
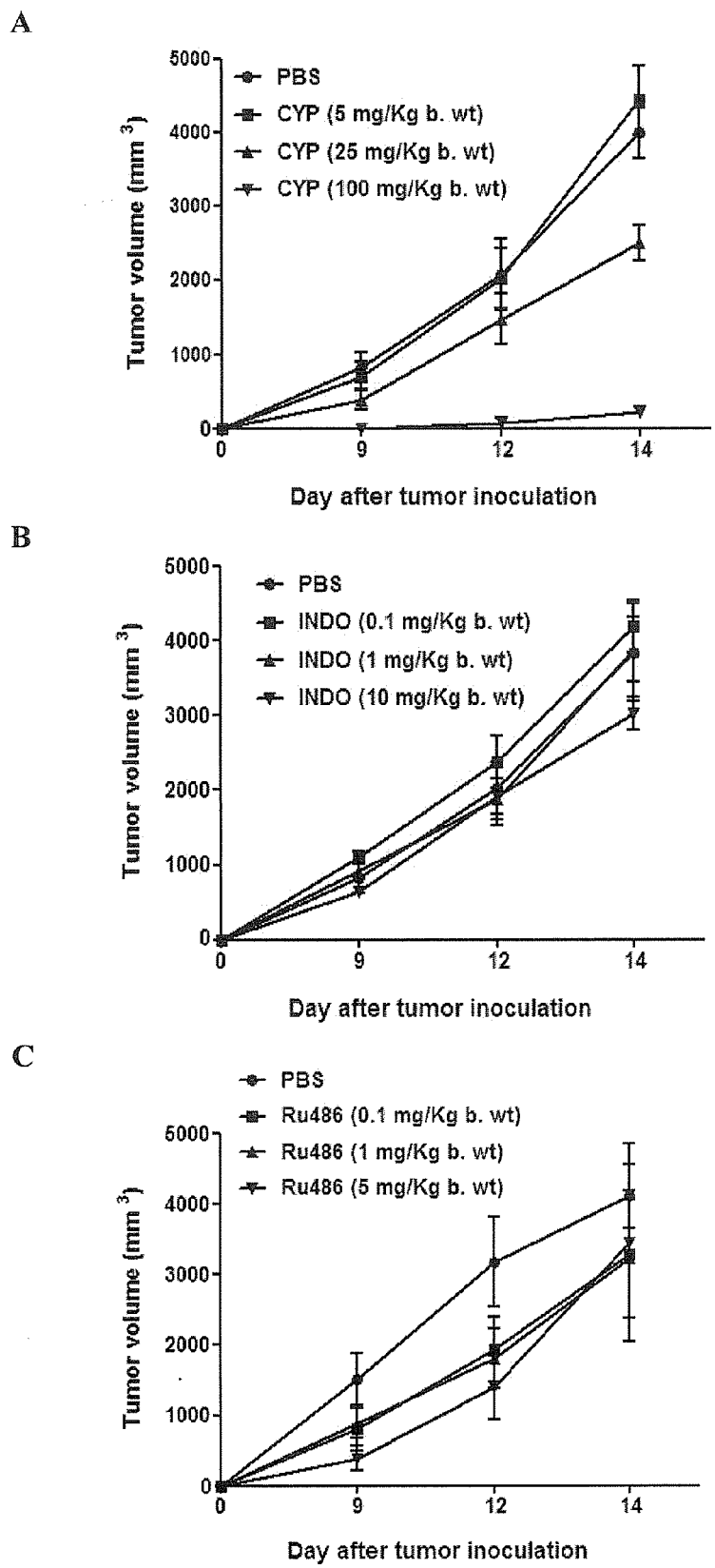

Since *Mycobacterium indicus pranii* is unable to completely prevent tumor progression when administered at 6 or even 3 days post-inoculation of Sp2/0 tumor cells, three different known anti-cancer drugs namely Cyclophosphamide, Indomethacin and RU486 are screened for their efficacy in reducing tumor volume. BALB/c mice are intraperitoneally injected with three different doses of Cyclophosphamide, Indomethacin and RU486 four days after implantation of Sp2/0 cells. The doses of Cyclophosphamide, Indomethacin and RU486 are chosen based on that administered to mice and the standardization of the same in the Sp2/0 tumor model is depicted in FIG. 4. BALB/c mice (5 per group) of 6 to 8 weeks of age are subcutaneously injected with Sp2/0 myeloma cells (~$10 \times 10^6$ cells/mouse). The mice are then intraperitoneally injected with different doses of either Cyclophosphamide (5, 15 or 100 mg/Kg body weight/mouse) or Indomethacin (0.1, 1 or 10 mg/Kg body weight/mouse) or RU486 (0.1, 1 or 5 mg/Kg body weight/mouse), 4 days post-inoculation of tumor cells. Tumor volume is estimated on the $9^{th}$, $12^{th}$ and $14^{th}$ day after tumor inoculation. Vehicle alone (0.5 ml of PBS) is used as control and intradermally injected 4 days after administration of cells.

It is observed that at the dose of 5 mg/Kg body weight, Cyclophosphamide is not able to reduce tumor progression, however at the dose of 100 mg/Kg body weight, Cyclophosphamide is able to prevent tumor progression to a considerable extent but the mice are affected i.e., reduced body weight and hair loss is seen. Moreover, in human beings, this dose when administered repeatedly is highly toxic. Indomethacin did not show any significant reduction in tumor volume even at the highest dose chosen whereas with RU486, a slight reduction is observed in the initial days which are lost at later stages. Although, none of the chemotherapeutic drugs significantly prevented tumor growth at the doses chosen, except cyclospahamide that is effective only at the highest dose. Intermediate dose values of the drugs [cyclophosphamide (15 mg/Kg b. wt), indomethacin (1 mg/Kg b. wt) and RU486 (1 mg/Kg b. wt.)] is selected as the most preferred concentration to evaluate the effect of the combination of *Mycobacterium indicus pranii* and drugs on tumor regression.

Example 5

Comparative Efficacy Between Different Drugs in Combination With *Mycobacterium Indicus Pranii* for the Treatment of Sp2/0 Myeloma Comparison is done on the effect of any of the three anti-cancer drugs Cyclophosphamide, Indomethacin or RU486 when administered along with *Mycobacterium indicus pranii* in BALB/c mice bearing Sp2/0 tumors. *Mycobacterium indicus pranii* is injected intradermally 3 days after Sp2/0 cell implantation and the drugs are injected via intra-peritoneal route the next day. Each of the anti-cancer drugs is administered at different effective doses, conventionally known to provide best possible results. Tumor volume is measured kinetically for monitoring the growth of Sp2/0 tumors. PBS is injected into control mice.

Figure 5:
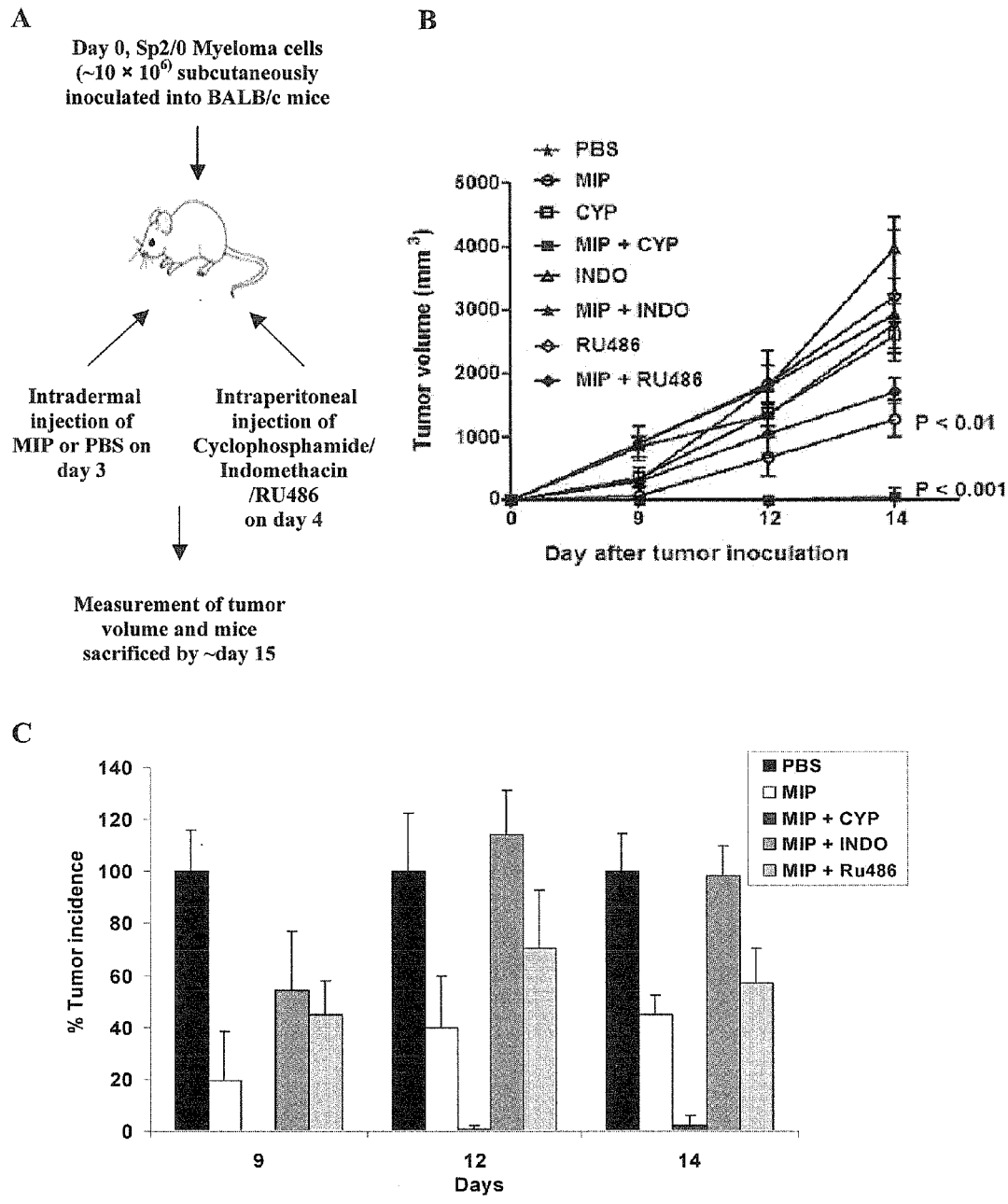

The comparative efficacy of the combination of different drugs and *Mycobacterium indicus pranii* in Sp2/0 myeloma bearing mice is depicted in FIG. 5. BALB/c mice (5 per group) of 6 to 8 weeks of age are subcutaneously injected with Sp2/0 myeloma cells (~$10 \times 10^6$ cells/mouse). Four groups of mice are intradermally injected with *Mycobacterium indicus pranii* (~$5 \times 10^8$) 3 days post-inoculation of tumor cells. Three groups of *Mycobacterium indicus pranii* injected mice are intraperitoneally injected with Cyclophosphamide (15 mg/Kg b. wt.), Indomethacin (1 mg/Kg b. wt.) and RU486 (1 mg/Kg b. wt.) on the next day. Tumor volume is estimated on the $9^{th}$, $12^{th}$ and $14^{th}$ after tumor inoculation. Vehicle alone (0.1 ml of PBS) is used as control and intradermally injected 3 days after administration of cells.

Intradermal injection of *Mycobacterium indicus pranii* is found to reduce the tumor size but Cyclophosphamide is able to induce an almost complete reduction in tumor volume in a synergistic manner. On the other hand, indomethacin seemed to reverse the beneficial effects observed with *Mycobacterium indicus pranii* and RU486 did not reduce tumor volume further compared to *Mycobacterium indicus pranii* alone. Overall, the data demonstrates that only Cyclophosphamide may induce substantial reduction in tumor size when given in combination with *Mycobacterium indicus pranii* for the treatment of myeloma in mice. The dose amount of 15 mg/Kg b. wt of Cyclophosphamide is the low non-toxic dose and is not able to sufficiently prevent tumor progression when administered individually, hence it is administered along with *Mycobacterium indicus pranii*. The Cyclophosphamide administration along with *Mycobacterium indicus pranii* is able to induce a synergistic reduction in tumor volume. The FIG. 5 also depicts that *Mycobacterium indicus pranii* individually can reduce tumor incidence considerably but the combination of Cyclophosphamide and *Mycobacterium indicus pranii* greatly retards tumor formation in mice.

Example 6

Comparative Efficacy of Different Doses of *Mycobacterium Indicus Pranii* with a Fixed Dose of Cyclophosphamide when Administered at an Early Stage of Tumor Next, the optimum dose of *Mycobacterium indicus pranii* required for reducing the tumor size in combination with Cyclophosphamide (15 mg/Kg b. wt.) and delaying the appearance of tumors is titrated. Comparative efficacy of different doses of *Mycobacterium indicus pranii* and cyclophosphamide in Sp2/0 myeloma bearing mice is provided in FIG. 6. BALB/c mice (3 per group) of 6 to 8 weeks of age are subcutaneously injected with Sp2/0 myeloma cells (~$10 \times 10^6$ cells/mouse). Mice are intradermally injected with different doses of *Mycobacterium indicus pranii* ($5 \times 10^3$, $5 \times 10^5$, $5 \times 10^7$ and $5 \times 10^8$) 3 days post-inoculation of tumor cells and then injected intraperitoneally with 15 mg/Kg b. wt. cyclophosphamide the following day. Tumor volume is estimated on the $9^{th}$, $12^{th}$ and $14^{th}$ day of tumor inoculation. Vehicle alone (0.1 ml of PBS) is used as control and intradermally injected 3 days after administration of cells. MIP alone dose dependently reduces tumor volume only at high doses ($5 \times 10^7$ and $5 \times 10^8$) but at low doses ($5 \times 10^3$ and $5 \times 10^5$) tumor volume is similar to that of PBS. Cyclophosphamide alone also showed some reduction in tumor volume. However, the combination of MIP and Cyclophosphamide reduced tumor volume compared to MIP alone at all the doses. The combination treatment at the highest dose of MIP ($5 \times 10^8$) led to an almost complete inhibition of tumor growth as two mice from the group did not develop tumors. Therefore, the maximal synergistic effect of *Mycobacterium indicus pranii* and cyclophosphamide on tumor volume reduction is observed when mice are administered with ~$5 \times 10^8$ *Mycobacterium indicus pranii*. Thus, the workable concentration range of MIP is about $5 \times 10^7$ to about $5 \times 10^9$, preferably about $5 \times 10^8$, when administered together with cyclophosphamide at early stage of tumor growth.

Example 7

Comparative Efficacy of Different Doses of Cyclophosphamide with a Fixed Dose of *Mycobacterium Indicus Pranii* when Administered at an Early Stage of Tumor Subsequently, the optimum dose of Cyclophosphamide required for reducing the tumor size in combination with *Mycobacterium indicus pranii* ($5 \times 10^8$) and delaying the appearance of tumors is titrated. Comparative efficacy of different doses of cyclophosphamide and *Mycobacterium indicus pranii* in Sp2/0 myeloma bearing mice is provided in FIG. 7. BALB/c mice (3 per group) of 6 to 8 weeks of age are subcutaneously injected with Sp2/0 myeloma cells (~$10 \times 10^6$ cells/mouse). Mice are intradermally injected with a fixed dose of *Mycobacterium indicus pranii* ($5 \times 10^8$) 3 days post-inoculation of tumor cells and then intraperitoneally injected with different doses of Cyclophosphamide (5, 15 or 50 mg/Kg body weight/mouse) next day. Tumor volume is estimated on the $9^{th}$, $12^{th}$ and $14^{th}$ day of tumor inoculation. Vehicle alone (0.1 ml of PBS) is used as control and intradermally injected 3 days after administration of cells. Cyclophosphamide at doses 1 and 5 mg/Kg b. wt. is unable to reduce tumor volume but MIP alone treatment significantly reduced tumor volume. The combined treatment of CYP (1 mg/Kg b. wt) and MIP did not show any effect on tumor volume and is even more than PBS which indicates that cyclophosphamide at this low dose might be inhibiting the antitumor effect of MIP. A clear reduction is seen with MIP and CYP (5 and 15 mg/Kg b. wt). Cyclophosphamide administered alone at 50 mg/Kg b. wt. is effective and further reduction is not achieved with combined therapy; however, at this dose Cyclophosphamide is toxic to mice. Thus, the workable non-toxic concentration range of cyclophosphamide is about 5 mg/Kg body weight to about 25 mg/Kg body weight, preferably about 15 mg/Kg body weight, when administered together with MIP at late stage of tumor growth.

Example 8

Comparison Efficacy of Cyclophosphamide Injected on Different Days in Combination with *Mycobacterium Indicus Pranii* on Sp2/0 Tumor Reduction in BALB/c Mice Next the optimal time of administration of Cyclophosphamide required for reducing the tumor size in combination with *Mycobacterium indicus pranii* ($5 \times 10^8$) and delaying the appearance of tumors is titrated. Comparative efficacy of different doses of cyclophosphamide and *Mycobacterium indicus pranii* in Sp2/0 myeloma bearing mice is provided in FIG. 8. BALB/c mice (3 per group) of 6 to 8 weeks of age are subcutaneously injected with Sp2/0 myeloma cells (~10×10$^6$ cells/mouse). Mice are intradermally injected with a fixed dose of *Mycobacterium indicus pranii* (5×10$^8$) 3 days post-inoculation of tumor cells and then intraperitoneally injected with different doses of Cyclophosphamide (5, 15 or 100 mg/Kg body weight/mouse) next day. Tumor volume is estimated on the 9$^{th}$, 12$^{th}$ and 14$^{th}$ day of tumor inoculation. Vehicle alone (0.1 ml of PBS) is used as control and intradermally injected 3 days after administration of cells. MIP treatment alone significantly reduced tumor volume but cyclophosphamide administered alone either on the same day as MIP or one day prior or one day after MIP, injection had no effect on tumor volume. In addition, the combination therapy with MIP and cycloposphamide given on the same day or prior to MIP is not able to reduce tumor volume. This clearly shows that injection of cyclophosphamide one day before or on the same day might be hampering the effect of MIP alone.

The best possible reduction in tumor size is achieved when MIP is given one day prior to cyclophosphamide, i.e., MIP three days and cyclophosphamide four days after inoculation of tumor cells.

Example 9

Effect of Combined Treatment of *Mycobacterium Indicus Pranii* and Cyclophosphamide in Reduction of Tumor Volume Cotherapy with *Mycobacterium indicus pranii* and Cyclophosphamide synergistically inhibits the growth of Sp2/0 myeloma in vivo. BALB/c mice (5 per group) of 6 to 8 weeks of age are injected subcutaneously with Sp2/0 myeloma cells (~10×10$^6$ cells/mouse). Two groups of mice are intradermally injected with *Mycobacterium indicus pranii* (~5×10$^8$) 3 days post-inoculation of tumor cells. Two groups of mice one injected previously with MIP and another uninjected are intraperitoneally injected with 15 mg/Kg body weight of Cyclophosphamide on the next day. Tumor volume is estimated in the three groups of mice on the 9$^{th}$, 12$^{th}$ and 14$^{th}$ day after tumor inoculation. This has been depicted in FIG. 9A. Vehicle alone (0.1 ml of PBS) is used as control and intradermally injected 3 days after administration of cells. The maximum reduction (~10 fold) in tumor volume is observed when mice are administered with *Mycobacterium indicus pranii* in combination with Cyclophosphamide in comparison to Phosphate Buffered Saline as shown in FIG. 9B. Further, FIG. 9C shows the pictographs depicting the size of the isolated subcutaneous solid myeloma tumors after treatment with PBS, *Mycobacterium indicus pranii*, Cyclophosphamide and a combination of *Mycobacterium indicus pranii* along with Cyclophosphamide.

These results clearly indicate that *Mycobacterium indicus pranii* can be safely used with Cyclophosphamide in a synergistic manner to delay the tumor progression. It is observed that the sequential combination of Cyclophosphamide and *Mycobacterium indicus pranii* improves the efficacy by 6 to 7 fold and about 80% to 90% reduction in tumor size is observed when compared to about 30% to 40% tumor reduction with Cyclophosphamide alone. All comparisons are done with mice injected with Phosphate Buffered Saline. Tumor volume which is usually drastically reduced and the effect eventually seen only at high doses of Cyclophosphamide is mimicked at a much lower dose when administered along with *Mycobacterium indicus pranii*. The other beneficial results are improved survival and better quality of life due to fewer toxic side-effects.

Blood is collected from anesthetized mice by cardiac puncture and allowed to clot 3 to 6 hours at room temperature (RT), then centrifuged for 10 minutes at 5000 rpm. Sera is collected and stored at −80° C. for cytokine analysis by enzyme-linked immunosorbent assay (ELISA) using kit manufactured by eBioscience. Cytokine concentrations are determined by comparison with a standard curve. The linear detection ranges of the cytokine assays are as follows: IFNγ, 15-2000 pg/ml; IL-4, 4-500 pg/ml; TGFβ, 2-200 pg/ml; IL-12p70, 15-2000 pg/ml; and IL-10, 30-4000 pg/ml; and TNFα, 8-1000 pg/ml, The FIG. 9D shows the cytokine production upon combination therapy of myeloma with *Mycobacterium indicus pranii* (~5×10$^8$) and Cyclophosphamide of concentration 15 mg/Kg body weight. The BALB/c mice are treated as mentioned above and mice are sacrificed on day 15. Serum is isolated from blood collected by cardiac puncture. Cytokine amounts in the serum are estimated by ELISA. Significance between *Mycobacterium indicus pranii* or *Mycobacterium indicus pranii*+Cyclophosphamide and PBS treated groups are indicated as follows: *, P<0.05; , P<0.01; *, P<0.001.

IL 12p70 and IFNγ levels are found to be higher and IL10, IL6, IL1β and TGFβ levels are lower in *Mycobacterium indicus pranii* and Cyclophosphamide treated mice compared to *Mycobacterium indicus pranii* alone. The positive effect of this combination therapy on tumor reduction may be due to enhancement of Th1 type cytokines and reduction of Th2 cytokines.

Example 10

Comparative Efficacy of Different Doses of *Mycobacterium Indicus Pranii* with a Fixed Dose of Cyclophosphamide when Administered at Later Stage of Tumor Cotherapy with *Mycobacterium indicus pranii* and Cyclophosphamide synergistically inhibits the growth of Sp2/0 myeloma in vivo when administered at an early stage of tumor progression. Since MIP effect is completely lost when administered at day 6 post-inoculation of tumor cells, the efficacy of the combination therapy is tested at a late stage when tumors have already developed. First, the optimum dose of *Mycobacterium indicus pranii* required for reducing the tumor size in combination with Cyclophosphamide (15 mg/Kg b. wt.) and delaying the appearance of tumors is titrated. Comparative efficacy of different doses of *Mycobacterium indicus pranii* in Sp2/0 myeloma bearing mice is provided in FIG. 10. BALB/c mice (3 per group) of 6 to 8 weeks of age are subcutaneously injected with Sp2/0 myeloma cells (~10×10$^6$ cells/mouse). Mice are intradermally injected with different doses of *Mycobacterium indicus pranii* (5×10$^3$, 5×10$^5$, 5×10$^7$ and 5×10$^8$) 7 days post-inoculation of tumor cells and then injected intraperitoneally with 15 mg/Kg b. wt. cyclophosphamide the following day. Tumor volume is estimated on the 11$^{th}$, 14$^{th}$ and 17$^{th}$ day of tumor inoculation. Vehicle alone (0.1 ml of PBS) is used as control and intradermally injected 7 days after administration of cells. MIP when administered alone at day 7 post-inoculation of sp2/0 cells, dose dependently induces a slight reduction in tumor volume but only at high doses (5×10$^7$ and 5×10$^8$). Cyclophosphamide alone also showed some reduction in tumor volume.

Combination of MIP and Cyclophosphamide significantly reduced tumor volume compared to MIP at the high doses ($5 \times 10^7$ and $5 \times 10^8$). Thus, the workable concentration range of MIP is about $5 \times 10^7$ to about $5 \times 10^9$, preferably about $5 \times 10^8$, when administered together with cyclophosphamide at late stage of tumor growth.

Example 11

Comparative Efficacy of Different Doses of Cyclophosphamide with a Fixed Dose of Mycobacterium Indicus Pranii when Administered at a Later Stage of Tumor Subsequently, the optimum dose of Cyclophosphamide required for reducing the tumor size in combination with *Mycobacterium indicus pranii* ($5 \times 10^8$) and delaying the appearance of tumors is titrated. Comparative efficacy of different doses of cyclophosphamide and *Mycobacterium indicus pranii* in Sp2/0 myeloma bearing mice is provided in FIG. 11. BALB/c mice (3 per group) of 6 to 8 weeks of age are subcutaneously injected with Sp2/0 myeloma cells ($10 \times 10^6$ cells/mouse). Mice are intradermally injected with a fixed dose of *Mycobacterium indicus pranii* ($5 \times 10^8$) 7 days post-inoculation of tumor cells and then intraperitoneally injected with different doses of Cyclophosphamide (5, 15 or 50 mg/Kg body weight/mouse) next day. Tumor volume is estimated on the $11^{th}$, $14^{th}$ and $17^{th}$ day of tumor inoculation. Vehicle alone (0.1 ml of PBS) is used as control and intradermally injected 7 days after administration of cells. MIP administered alone on day 7 post-inoculation of Sp2/0 cells did not significantly reduce tumor volume nor did cyclophosphamide alone at low doses i.e. 1, 5 and 15 mg/Kg b. wt. Combined therapy with Cyclophosphamide and MIP at low doses (1, 5 mg/Kg b. wt) also did not show significant reduction in tumor volume compared to MIP or cyclophosphamide alone at these doses. Significant reduction in tumor volume is achieved when MIP is administered with cyclophosphamide at the dose of 15 mg/Kg b. wt. Cyclophosphamide at the highest dose (50 mg/kg) is otherwise toxic to mice though it resulted in significant tumor reduction. Thus, the workable concentration range of cyclophosphamide is about 5 mg/Kg body weight to about 25 mg/Kg body weight, preferably about 15 mg/Kg body weight, when administered together with MIP at late stage of tumor growth.

Example 12

Effect of Combined Treatment of Mycobacterium Indicus Pranii and Cyclophosphamide in Reduction of Tumor Volume BALB/c mice (5 per group) of 6 to 8 weeks of age are injected subcutaneously with Sp2/0 myeloma cells (~$10 \times 10^6$ cells/mouse). Two groups of mice are intradermally injected with *Mycobacterium indicus pranii* (~$5 \times 10^8$) 7 days post-inoculation of tumor cells. Two groups of mice one injected previously with MIP and another uninjected are intraperitoneally injected with 15 mg/Kg body weight of Cyclophosphamide on the next day. Tumor volume is estimated in the three groups of mice on the $11^{th}$, $14^{th}$ and $17^{th}$ day after tumor inoculation. This has been depicted in FIG. 12. Vehicle alone (0.1 ml of PBS) is used as control and intradermally injected 7 days after administration of cells. The efficacy of MIP is lost whereas Cyclophosphamide alone is unable to induce any effect on tumor reduction; in fact, the tumor size is comparable to PBS on the day when the mice are sacrificed. However, the combined therapy of cyclophosphamide and MIP synergistically reduced tumor volume even when administered at the later stages of tumor progression.

Example 13

Efficacy of Cyclophosphamide Given in Combination with MIP at an Early or Advanced Stage of EL4 Tumor Progression in C57BL/6 Mice The efficacy of the synergistic combination of *Mycobacterium indicus pranii* and Cyclophosphamide is also verified in another aggressive tumor model i.e. EL4 thymoma. EL4 cells, a thymoma cell line, is grown in T75 flasks in RPMI complete medium supplemented with 10% fetal bovine serum, 2 mM L-glutamine, 100 U/ml penicillin, 100 μg/ml streptomycin, 10% nonessential amino acids, 10% HEPES, 10% sodium pyruvate, 50 μM 2-ME, 10 μg/ml gentamycin in a humidified atmosphere of 5% $CO_2$ at 37° C.

C57BL/6 mice (5 per group) of 6 to 8 weeks of age are injected subcutaneously with EL4 myeloma cells (~$0.5 \times 10^6$ cells/mouse). Two groups of mice are intradermally injected with *Mycobacterium indicus pranii* (~$5 \times 10^8$) either 3 or 7 days post-inoculation of tumor cells. Two groups of mice one injected previously with MIP and another uninjected are intraperitoneally injected with 15 mg/Kg body weight of Cyclophosphamide on the next day. Tumor volume is estimated in the three groups of mice on the $11^{th}$, $14^{th}$ and $17^{th}$ day after tumor inoculation. This has been depicted in FIG. 13. Vehicle alone (0.1 ml of PBS) is used as control and intradermally injected 7 days after administration of cells.

MIP is able to reduce tumor volume but its efficacy is lost when administered at later time. Cyclophosphamide alone is unable to induce any effect on tumor reduction; in fact, the tumor size is greater than observed with PBS when administered on day 8. Tumor volume is significantly reduced by combined therapy with cyclophosphamide and MIP at both the early and later stages of tumor progression.

The increase in IL 12p70 or IFNγ amounts that is seen upon MIP treatment alone is not observed when administered on day 7. On the contrary, the decrease IL6 and TGFβ amounts observed with MIP alone is the same irrespective of the day of injection but IL1β and IL10 amounts are more when treatment with MIP is delayed. IL12p70 and IFNγ amounts are increased and IL6, TGFβ, IL1β and IL10 amounts are significantly reduced in the combination treated groups, irrespective of the day of injection. However, the extent of increase or decrease depending on the cytokines is somewhat less when the combination is injected at the later stage than at the early stage of tumor progression.

CONCLUSION

The synergistic combination of Cyclophosphamide and *Mycobacterium indicus pranii* is administered to mice detected with B-cell malignancies such as Multiple myeloma, Solitary plasmacytoma and Plasma cell leukemia. The experiment is conducted mainly on mice which have been detected with said myelomas. The mice are initially examined and the tumor growth and size approximately determined. The mice are then divided into groups so that 5 mice form a group. One mice group is subjected to only *Mycobacterium indicus pranii* treatment and another group to only Cyclophosphamide treatment. The third group of mice is subjected to a treatment of *Mycobacterium indicus pranii* along with Cyclophosphamide. This third group of mice are initially intradermally injected with *Mycobacterium indicus pranii* at a concentration range of ~$5 \times 10^8$ cells. Thereafter, the same mice are intraperitoneally injected with 15 mg/Kg body weight of Cyclophosphamide on the next day. The mice are then re-examined and the tumor volume estimated on different days after *Mycobacterium indicus pranii* administration.

The tumor volume in each mice group is observed to decrease in size, when compared with the tumor size values initially observed. However, in comparison the third mice group subjected to a combination of *Mycobacterium indicus pranii* and Cyclophosphamide depicted extraordinary reduction in the tumor size/volume. The non-toxic dose of Cyclophosphamide or *Mycobacterium indicus pranii* individually failed to elicit a similar tumor size reduction. About 80% to 90% reduction in tumor size is observed in the third group of mice when compared with about 30% to 40% tumor size reduction observed with Cyclophosphamide alone.

The present disclosure specifically provides a method for the treatment of different forms of myeloma by sequential administration of a therapeutically effective dose of heat killed *Mycobacterium indicus pranii* followed by the administration of a known chemotherapeutic drug: Cyclophosphamide a day after. Both *Mycobacterium indicus pranii* and Cyclophosphamide have individually been safely administered to humans. *Mycobacterium indicus pranii* is used as an immunomodulator and Cyclophosphamide is used as a chemotherapeutic drug. However, use of chemotherapeutic drugs like Cyclophosphamide results in toxic side-effects, high Cyclophosphamide doses are often seen to be highly toxic and the lower non-toxic doses of Cyclophosphamide are not effective. The present disclosure relates to a mode of improving the efficacy of non-toxic doses of Cyclophosphamide by providing it along with heat-killed *Mycobacterium indicus pranii*. Particularly, the present disclosure involves the administration of low non-toxic doses of Cyclophosphamide, which acts in a synergistic manner with *Mycobacterium indicus pranii* when they are sequentially administered. The sequential administration of *Mycobacterium indicus pranii* and Cyclophosphamide results in substantial reduction in tumor volume immunotherapeutically.

We claim:

1. A kit for treating lymphoma, said kit comprising a synergistic sequential combination of *Mycobacterium indicus pranii* (MIP) at a concentration ranging from $5 \times 10^7$ to about $5 \times 10^9$ of *Mycobacterium* cells and Cyclophosphamide at a dose ranging from about 5 mg/Kg body weight to about 25 mg/Kg body weight.

2. The kit as claimed in claim 1, wherein the *Mycobacterium indicus pranii* is heat killed bacteria at a concentration of about $5 \times 10^8$ of *Mycobacterium* cells; and the Cyclophosphamide is at a non-toxic low dose of about 15 mg/Kg body weight.

3. The kit as claimed in claim 1, wherein the kit further contains pharmaceutically acceptable excipients and instruction manual.

4. A method of treating lymphoma, said method comprising the step of administering a synergistic sequential combination comprising *Mycobacterium indicus pranii* (MIP) and Cyclophosphamide to a subject in need thereof; wherein the *Mycobacterium indicus pranii* (MIP) is at a concentration ranging from $5 \times 10^7$ to about $5 \times 10^9$ of *Mycobacterium* cells and is administered about 24 hours prior to administering Cyclophosphamide at a dose ranging from about 5 mg/Kg body weight to about 25 mg/Kg body weight.

5. The method as claimed in claim 4, wherein the subject is a mammal including a human being.

6. The method as claimed in claim 4, wherein the *Mycobacterium indicus pranii* is heat killed bacteria at a concentration of about $5 \times 10^8$ of *Mycobacterium* cells; and wherein the Cyclophosphamide is at a non-toxic low dose of about 15 mg/Kg body weight.

7. The method as claimed in claim 4, wherein the *Mycobacterium indicus pranii* is administered intradermally and the Cyclophosphamide is administered intraperitoneally.

8. The method as claimed in claim 4, wherein the lymphoma is selected from a group comprising Myeloma and Thymoma.

9. The method as claimed in claim 4, wherein the lymphoma's size is reduced by about 80% to about 90%.

* * * * *